United States Patent [19]

McGaffigan

[11] Patent Number: 5,676,784
[45] Date of Patent: Oct. 14, 1997

[54] METHOD OF FABRICATING A HEATER COIL FOR A CATHETER USED TO MONITOR CARDIAC OUTPUT

[75] Inventor: Thomas Haynes McGaffigan, Saratoga, Calif.

[73] Assignee: Abbott Laboratories, Abbott Park, Ill.

[21] Appl. No.: 404,893

[22] Filed: Mar. 15, 1995

[51] Int. Cl.$^6$ .................... B65H 81/00; B32B 31/00; H05B 3/00; B23P 11/02
[52] U.S. Cl. .................... 156/172; 29/611; 29/447; 128/713; 156/172; 156/274.2
[58] Field of Search ............ 29/611, 447; 128/713, 128/691; 607/115, 122; 604/113, 114; 174/47; 156/86, 187, 194, 195, 172, 274.2, 309.6

[56] References Cited

U.S. PATENT DOCUMENTS

| | | |
|---|---|---|
| 3,075,515 | 1/1963 | Richards . |
| 3,359,974 | 12/1967 | Khalil . |
| 3,412,354 | 11/1968 | Sattler ............................ 29/605 |
| 3,568,660 | 3/1971 | Crites et al. ..................... 607/122 |
| 4,559,951 | 12/1985 | Dahl et al. ...................... 607/122 |
| 4,619,643 | 10/1986 | Bai . |
| 5,056,526 | 10/1991 | Khalil . |
| 5,265,623 | 11/1993 | Kroll et al. ..................... 607/122 |
| 5,335,410 | 8/1994 | Burnham . |
| 5,476,562 | 12/1995 | Inhofe, Jr. ....................... 156/172 |

FOREIGN PATENT DOCUMENTS

| | | |
|---|---|---|
| 0456342 | 11/1991 | European Pat. Off. . |
| 9113648 | 9/1991 | WIPO . |

OTHER PUBLICATIONS

Search Report PCT/US 96/01996.

*Primary Examiner*—P. W. Echols
*Attorney, Agent, or Firm*—Neal D. Marcus; Ronald M. Anderson

[57] ABSTRACT

A heater (12) for a catheter (10) used in monitoring constant cardiac output is fabricated using a bifilar wire (21) coated with polyvinyl chloride (PVC) like the material used for the catheter. The bifilar wire is coated with the PVC using a conventional extrusion technique, producing a coated lead (24, 32). This coated lead is wrapped around the exterior surface of the catheter, forming a helical coil. Heat is applied to the coated lead to melt the PVC coating, causing it to bond the lead to the catheter. The melted PVC also flows into gaps (23) or notches between adjacent coils of the lead, producing a relatively smooth outer surface for the heater coil when the PVC coating cools. The bifilar wire can alternatively be wrapped in-line with PVC tape (29) or film and the PVC material heated to flow around the wire, bonding it to the catheter's outer surface.

26 Claims, 4 Drawing Sheets

METHOD OF FABRICATING A HEATER COIL FOR A CATHETER USED TO MONITOR CARDIAC OUTPUT

FIELD OF THE INVENTION

The present invention generally pertains to a catheter used to monitor the rate at which blood is pumped from the heart, and more specifically, to a heater that is used on such a catheter for heating the blood in the heart so that the cardiac output can be determined.

BACKGROUND OF THE INVENTION

Various techniques are used for determining the volumetric output of a patient's heart, i.e., the rate at which blood is pumped from the heart. One technique that is used requires that a bolus of chilled saline solution be injected into the heart through an intracardial catheter. By measuring the change in the temperature of the blood leaving the heart, the volumetric flow rate (cardiac output) can be determined.

It will be apparent that the preceding technique for determining cardiac output cannot be used on a continuous basis. An alternative technique, which enables continuous monitoring of cardiac output, involves heating the blood in a chamber of the heart and then monitoring the temperature of the blood downstream of the chamber. The preferred method for heating the blood is with an electrical heating element that is disposed on the outer surface of a catheter, near its distal end. The catheter is threaded through the patient's cardiovascular system, and the heater section of the catheter is positioned in the desired cardiac chamber. Small gauge leads disposed in one of the lumens of the catheter convey electrical current from an external power source to the heating element. This heating element warms the blood in the chamber when the heater is energized, so that cardiac output can be monitored on a continuous basis.

Because the catheter must be threaded through a patient's cardiovascular system, the heater element formed on the outer surface of the catheter must be relatively compact; it cannot add significantly to the diameter of the catheter. Furthermore, the heater element must have a smooth outer surface so that it can pass freely through blood vessels.

To form a heating element on the outer surface of the catheter, the previous technique provided for drawing a bifilar wire from which the heating element is formed through a syringe that contains a thermal-set polyurethane resin. The bifilar wire comprises two adjoined insulated copper conductors, each provided with nylon (or other plastic) insulation jackets by which they are adjoined. When drawn from the syringe, the bifilar wire is covered with liquid polyurethane and is coiled around the catheter while wet with this coating. Each of the conductors comprising the coiled bifilar wire is electrically joined to one of two leads; these leads are extended to the proximal end of the catheter through one of its lumens. The connections between the leads and the bifilar wire conductors are separately insulated and forced back inside the catheter lumen.

The polyurethane coating is thermally cured at an elevated temperature for about 48 hours. To minimize the diameter of the heating element, the bifilar wire is wound in a single layer with the two conductors comprising the wire running side-by-side. The distal ends of the bifilar conductors are connected together to form a series circuit. Current flows in opposite directions in adjacent conductors of the wire comprising the heater element. Any magnetic field caused by current flowing in one of the two conductors of the bifilar wire cancels that caused by the current flowing in the other conductor.

There are several problems in fabricating a heater element for a constant cardiac output catheter in the manner described above. The process requires skilled hand labor and is therefore expensive. In addition, during the relatively long time (48 hours) required for the thermal-set polyurethane to cure, the resin, although viscous, remains sufficiently fluid to flow around the catheter, forming a thickened slump on the lower side of the catheter. Consequently, the polyurethane coating on the heater coils is non-uniform in thickness. Before the resin sets, it is very tacky and tends to pickup dust motes and other undesirable pyrogens from the environment. In addition, irregularities and bumps in the resin can cause the surface to be too rough. Accordingly, it will be evident that a more efficient technique is desired to fabricate the heater element and bond it to the catheter. The new method should produce a consistently smooth and regular surface on the exterior of the heater element. Furthermore, the new method should enable the heater element to be produced with a minimum of hand labor and should eliminate the long cure time that is presently required.

SUMMARY OF THE INVENTION

In accordance with the present invention, a method is defined for making a heater for a catheter that is employed to monitor cardiac output. The method includes the steps of providing a catheter having at least one lumen adapted to accept a heater lead. A wire that will be used for forming the heater is coated with a thermoplastic material to form a coated lead. The coated lead is wound around the catheter to form a heater coil. When the heater coil is formed, it includes gaps defined between adjacent coils of the coated lead. The temperature of the heater coil is then elevated, melting the thermoplastic material, causing the material to flow into and fill the gaps between the adjacent coils of the coated lead and bonding the heater coil to the catheter.

In one preferred form of the invention, the adjacent coils of the coated lead do not contact each other when the heater coil is wound. When the thermoplastic material melts, the material flows into and fills the gaps to form a generally smooth outer surface on the heater coil.

In another embodiment, the adjacent coils of coated lead contact each other when the heater coil is wound. The gaps each comprise notches disposed adjacent the surface of the catheter and outwardly of each point where the coils of coated lead contact each other. When the thermoplastic material melts, the material flows into the notches to form a generally smooth outer surface on the heater coil.

In one embodiment, the coated lead has a generally circular cross-sectional shape. In another embodiment, the coated lead has a generally quadrilateral cross-sectional shape. Preferably, the wire comprises a bifilar wire with two adjacent conductors.

Another embodiment of the invention provides for wrapping the plastic material around the coils of the wire. Preferably, the plastic material is wound with the wire in line forming layers of the plastic material and wire so that when the plastic material is heated, it flows, attaching the coils of wire to the outer surface of the catheter and providing a substantially smooth surface.

Another aspect of the present invention is directed to using a heat-shrink tube to form the plastic material on the wire. Heat applied to the heat-shrink is conveyed through the heat-shrink tube, melting the plastic material on the wire. The heat-shrink tube shrinks around the coils of wire to form the plastic material as it is melted. After the plastic material cools, the heat-shrink tube is removed.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
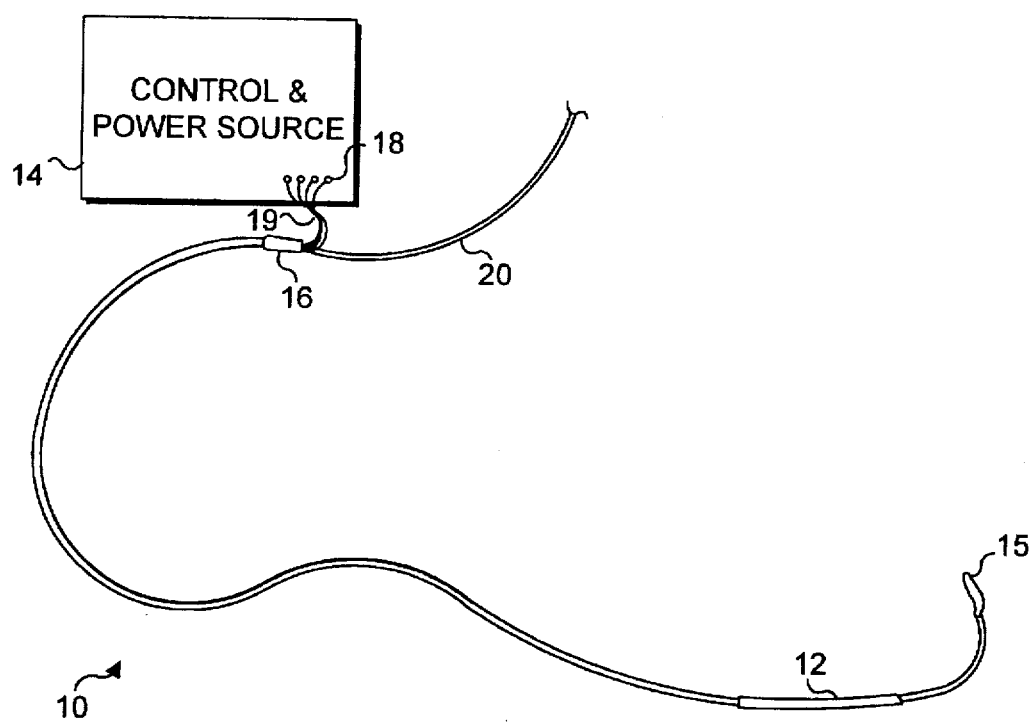
FIG. 1 is a block diagram that shows a catheter having a heater element fabricated in accord with the present invention and a control and power source for the heater element.

Referring to FIG. 1, a catheter 10 of the type used for monitoring constant cardiac output, and a control and power source 14 for the catheter are schematically shown. Catheter 10 includes a heater 12 that is fabricated in accord with the present invention. At the distal end of catheter 10 is disposed a balloon 15, which can be inflated after the catheter has been positioned within a patient's heart to ensure that the distal end of the catheter is carried out of the right ventricle, into the pulmonary artery. When preparing to continuously monitor a patient's cardiac output, catheter 10 is typically inserted into a patient's body through a slit in an appropriate artery, threaded through the cardiovascular system into the right atrium of the heart, and passed into the right ventricle. Balloon 15 is then inflated, carrying the distal end of the catheter out of the heart and into the pulmonary artery. The distal end of catheter 10 includes a thermister (not shown) or other temperature sensor for monitoring the change in the temperature of the blood leaving the heart as it is heated inside the right ventricle by heater 12. Based upon the temperature change of the blood and the amount of heat added, the volumetric rate of blood flow from the patient's heart (cardiac output) can be continuously monitored. Control and power source 14 supplies the electrical power to heater 12 and monitors the change in temperature of the blood to determine the cardiac output. Since the method employed in using catheter 10 to determine cardiac output is not the subject of this invention, there is no need for a more detailed explanation of the process.

A sheath 16 encloses the proximal end of catheter 10 at a point where a plurality of electrical leads 19 emerge to connect to terminals 18 on control and power source 14. Two of electrical leads 19 convey electrical current to heater 12 through a lumen (not shown) in catheter 10, from control and power source 14; the remaining leads, which are conveyed through other lumens of the catheter, are used in connection with monitoring the temperature of blood within the heart and within the pulmonary artery. A fluid line 20 extends from the proximal end of catheter 10 and can be coupled to a source of pressurized fluid for inflating balloon 15. Additional fluid lines coupled to other lumens of catheter 10 can be included to convey fluids into the heart through openings within the catheter adjacent its distal end.

Figure 2:
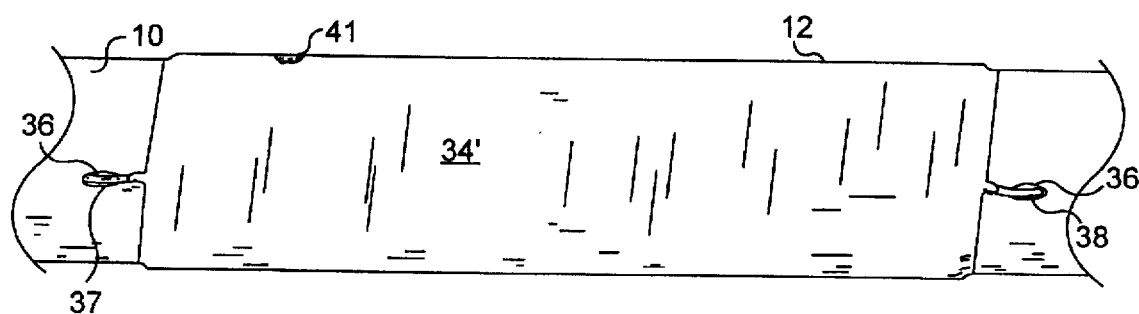
FIG. 2 is an elevational view showing a section of the catheter illustrated in FIG. 1 on which the heater element is disposed.
Figure 8:
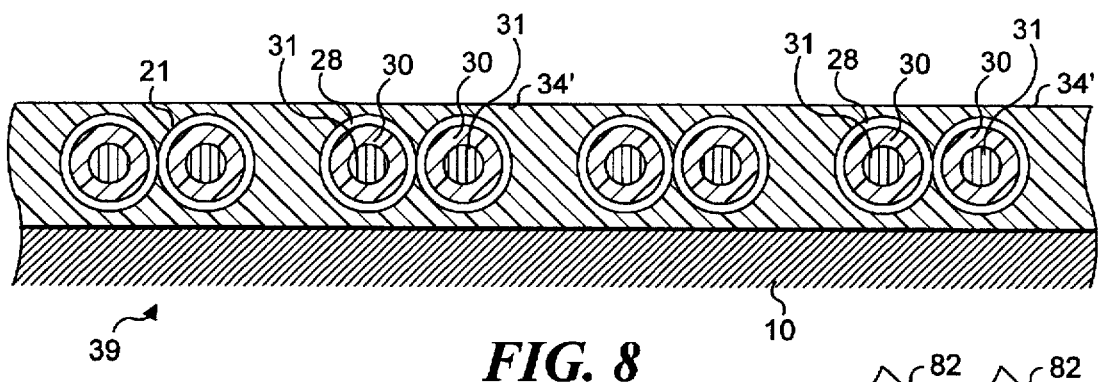
FIG. 8 is a cross-sectional view of the embodiment shown in FIG. 7, after heat has been applied to melt the coating.

FIG. 2 illustrates a portion of catheter 10 upon which heater 12 is disposed and shows further details of its construction. Although heater 12 appears to substantially increase the diameter of catheter 10 as illustrated in FIGS. 1 and 2, in reality, the heater adds very little to the cross-sectional size of the catheter. With reference to FIG. 2, it will be noted that the two leads, which convey electrical current to heater 12, are separately connected to the heater at insulated junctions 37. The junctions are then pushed back into the lumen that conveys the leads, through an opening 36. At the distal end of the heater, a termination 38 of the leads comprising the heater is similarly forced into an opening 36 within the lumen. Openings 36 are subsequently sealed. In the preferred embodiment of heater 12 in FIG. 2, the outer surface of the heater comprises a heat fusion bonded polyvinyl chloride (PVC) coating 34', which is relatively free of bumps or other surface irregularities. A small cut-away section 41 shows the conductors comprising the heater. A more detailed view of this embodiment is shown in FIG. 8.

Figure 3:
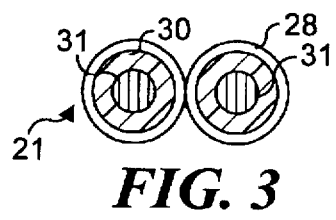
FIG. 3 is a cross-sectional view of a bifilar wire of the type used in the present invention.

Heater 12 is preferably fabricated using a bifilar wire 21 comprising two side-by-side conductors 31, as shown in FIG. 3. Each of conductors 31 comprises type C110 copper and is 39 AWG (about 0.0035 inches in diameter). A polyester insulation layer 30 surrounds each of conductors 31 and is approximately 0.0008 inches thick (measured in the radial direction). Surrounding the polyester insulation layer and bonding conductors 31 together in the side-by-side configuration is a film of NYLON™ 28 that is approximately 0.000025 inches thick (also measured in the radial direction). Based upon the dimensions recited above, it should be apparent that bifilar wire 21 is remarkably small in cross-sectional size. The greatly enlarged cross section of the bifilar wire shown in FIG. 3 is therefore somewhat misleading.

Figure 4:
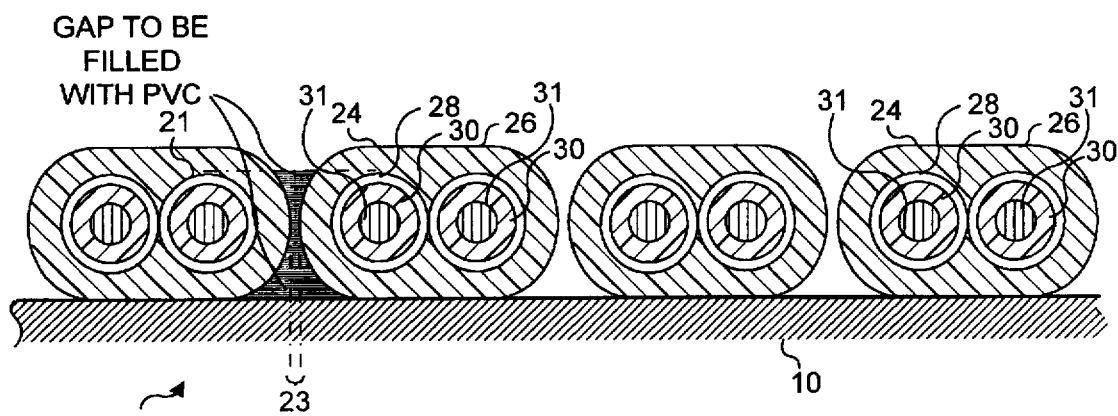
FIG. 4 is a cross-sectional view of several adjacent coated bifilar wires on an outer surface of a catheter, before heat is applied to the wire to melt the coating.

To fabricate specific preferred embodiments of heater 12, bifilar wire 21 is processed through an extruder to provide it with a PVC coating 26, forming a coated lead 24, as shown in an embodiment 22, for example, in FIG. 4. A generally conventional extrusion process like that used to apply an insulating coating to electrical wire is used to produce the coated lead. In one preferred embodiment, PVC coating 26 comprises the same type of PVC as the material from which catheter 10 is fabricated. Thus, the PVC comprising catheter 10 and PVC coating 26 have identical characteristics, so that heat fusion bonding is enhanced and biocompatability is assured. In another preferred embodiment, the melt temperature of PVC coating 26 is less than the melt temperature of catheter 10. However, bonding between the catheter surface and the PVC coating on the wire still occurs.

In the next step in the process of fabricating heater 12, coated lead 24 is helically wrapped around an exterior surface of catheter 10 at the point where the heater is to be formed; the successive wraps of the coated lead thus produce a closely spaced helical coil around the catheter. Only a small portion of the heater, along one side of the catheter is shown in FIG. 4. When the coated lead is wrapped around the catheter, a small gap 23 may be provided between the facing surfaces of adjacent coils. The dimension of gap 23 is carefully controlled to ensure that when PVC coating 26 is heated above its characteristic melting temperature, the molten PVC coating comprising the radially outer surface of coated leads 24 will flow into and completely fill the void between the adjacent coils, with a minimum movement of material. The required size of the gap is determined by calculating the total void area between adjacent coils of coated lead 24, which varies with the size of gap 23, and selecting a gap size that yields a void area approximately equal to the area of PVC coating 26 that radially overlies the outer surface of bifilar wire 21. For example, in FIG. 4, the void area that must be filled between two adjacent coils of coated lead is shown by the closely spaced horizontal lines, and the PVC coating that is available to fill the void area is disposed above the horizontal dash-dot-dash line that extends over this void area. Gap 23 is maintained at this selected value between successive coils of coated lead 24 so that the cross-sectional area of void between the coils is equal (or slightly less than) the area of the PVC coating covering the radially outer portion of the coated leads.

Figure 5:
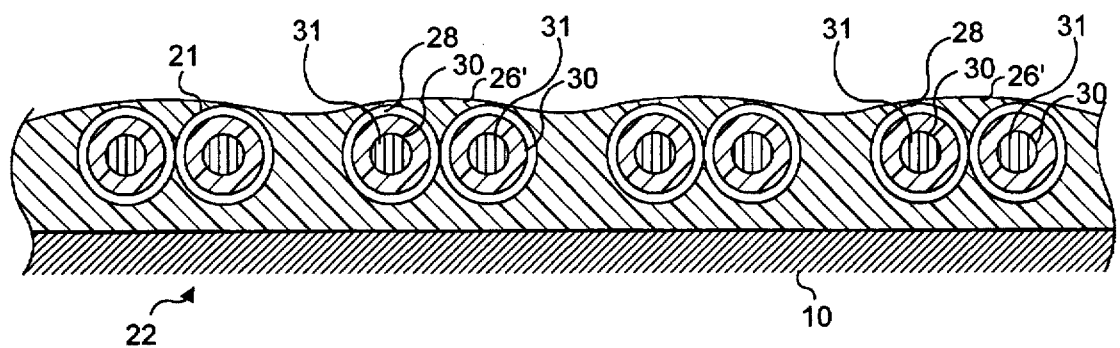
FIG. 5 is a cross-sectional view like that of FIG. 4, showing the coated bifilar wires after heat is applied to melt the coating.

FIG. 5 shows how embodiment 22 appears after the PVC coating of the coated lead is heated above its characteristic melting temperature and forced to flow into gap 23. As shown in this Figure, most of the PVC coating on the top surface (radially outer surface) of the coated lead has melted and flowed into the void between adjacent coils of the coated lead, completely filling that space and substantially reducing the total thickness of heater 12. The outer surface of PVC coating 26' in embodiment 22 is relatively smooth, having only minor ripples formed over each bifilar wire coil. When PVC coating 26 melts, it flows into the voids between adjacent wraps of coated wire 24 and bonds with the outer surface of catheter 10. With regard to one technique for forming the melted PVC coating, the outer surface formed on heater 12 is dependent upon the surface finish of a channel 48 in a die 40 (shown in FIG. 11 and discussed below) in which the coating is heated and is substantially smoother and much more regular than that produced by the prior art technique used to form a heater from a wire coated with a thermal-set polyurethane coating. In the prior art technique, the polyurethane coating was subject to slumping due in part to the long cure time and the effects of gravity flow, producing a bumpy surface, thin on one side and thick on the other. In contrast, the PVC coating used in the present invention is reflowed, bonded, and cooled within minutes, yielding a relatively smooth surface that is of substantially constant thickness.

Three very different techniques can be employed to melt PVC coating 26 on coated lead 24 and bond the coated lead to the catheter. The first technique uses the inherent resistance of the coil assembly in combination with electrical current flow through it to heat the PVC coating above its melting temperature. Conductors 31 in the bifilar wire are electrically coupled together at the distal end of the heater. Next, a source of electrical current is coupled to the proximal end of the conductors (or to leads 19 if junction 36 has already been fabricated). In the preferred embodiment, a direct current (DC) voltage is applied to the heater at a level selected to cause approximately four amps to flow through conductors 31 for ten to fifteen seconds. Because of the relatively small gauge of conductors 31 in bifilar wire 21, the current quickly heats the PVC coating above its melting point, causing it to flow into the voids between adjacent wraps of the coated lead. Alternatively, a high-frequency alternating current (AC) of approximately one amp at 200 kHz can be applied to the heater for ten to fifteen seconds. Less current is required for heating at this high frequency due to the higher effective resistance of the heater. At this frequency, the AC tends to flow along the outer surface of conductors 31 due to the "skin effect." Heating of the coating with electrical current flowing through the wire is more efficient than heating with an external heat source.

Figure 11:
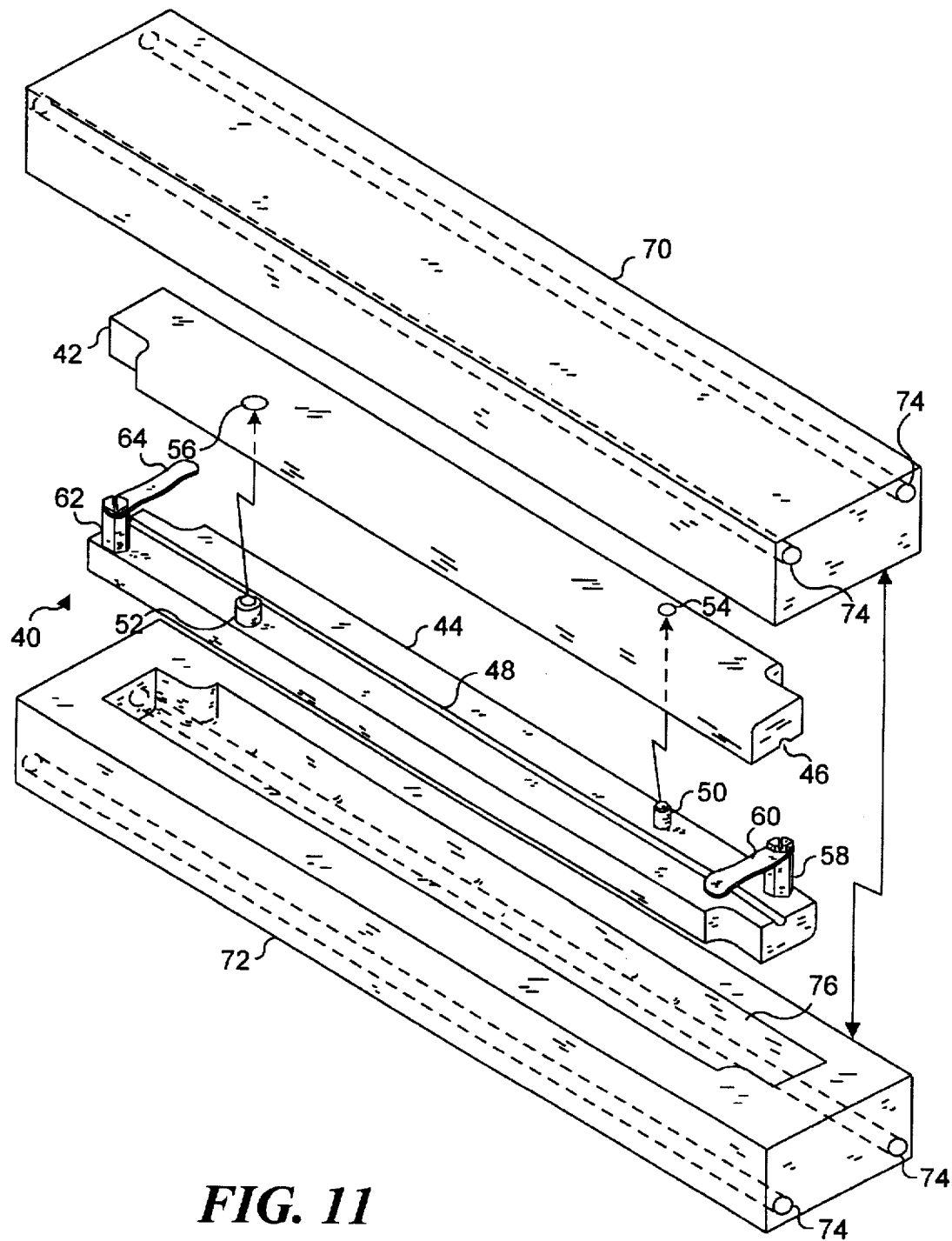
FIG. 11 is an isometric view showing two portions of a die (split apart) in which the section of the catheter on which the coated bifilar winding is coiled is held when the coating is heated.

However, coated lead 24 can also be heated using externally applied heat. Preferably, die 40, which is shown in FIG. 11, is used in heating PVC coating 26 above its melting temperature. Die 40, includes two mating die sections 42 and 44. The section of catheter 10 wrapped with the helical coils of coated lead 24 is positioned within a channel 48 that extends longitudinally along the upper surface of die section 44. Die 40 is sufficiently long so that the section of catheter 10 on which coated lead 24 is wrapped fits between the ends of the channel. Die section 42 includes a corresponding channel 46 running longitudinally along its lower surface. On the upper surface of die section 44 are disposed dowel pins 50 and 52. The dowel pins are slightly inset from the outer edges of the upper surface and are inset from the ends of the die section. Dowel pin 52, which is larger in diameter than dowel pin 50, is sized to fit within an orifice 56 that extends through die section 42. Likewise, dowel pin 50 is sized to fit within a corresponding orifice 54 formed in die section 42.

Die section 42 is fitted into mating engagement with die section 44, locking the section of catheter 10 on which the heater is wound within channels 46 and 48. An upright post 58 attached to the upper surface of die section 44, adjacent one end, supports a rotatable leaf spring clip 60. Similarly, an upright post 62, which is disposed on the upper surface of die section 42, adjacent its other end, supports a rotatable leaf spring clip 64. After the two die sections are coupled together around the catheter, leaf spring clips 60 and 64 are rotated to overlie the upper surface of die section 42, applying a force that clamps die section 42 against die section 44.

Once the section of catheter 10 on which coated lead 24 is wrapped is thus clamped in place within die 40, two heated blocks 70 and 72 having pockets 76 formed to fit over die 40 from opposite sides are brought together to enclose the die 40. The heated blocks include passages 74 into which cartridge heaters (not shown) are inserted. The cartridge heaters, which have previously been energized for some time, heat the two-to-three pound mass of aluminum comprising the heated blocks to approximately 140° C. Heated blocks 70 and 72 are clamped in contact with die 40 for approximately ninety seconds, during which time heat is transferred to the die and thus to the PVC coating on the coated lead wrapped around the catheter to raise the PVC coating above its melting point. Immediately thereafter, the two heated blocks are removed, and two cooled blocks (not shown) of approximately the same size and mass and having identical pockets to accommodate die 40 are clamped around the die. The cooled blocks, which have previously been cooled to approximately 0° C., by passing a chilled fluid through passages within the blocks, draw heat from die 40, quickly cooling and solidifying the melted PVC coating.

The PVC coating on the coated lead that was melted by heat transferred from the heated blocks is thus bonded to the outer surface of catheter 10 and will have flowed into the gaps or notches between adjacent wraps of the coated lead. In a production run, the blocks used to heat and cool die 40 at spaced-apart points on an assembly line will likely be moved to enclose die 40 by hydraulic or mechanical rams, to automate the process.

Figure 9:
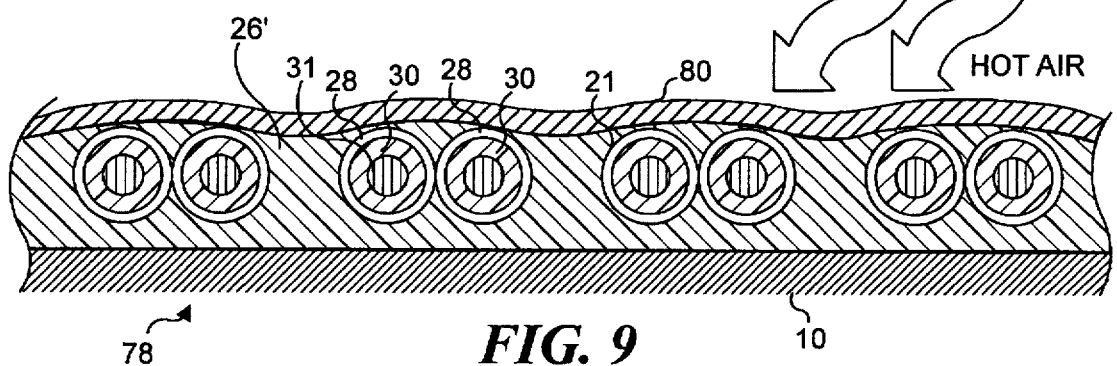
FIG. 9 is a cross-sectional view of another embodiment in which a heat-shrink tube is fitted over the helically coiled coated bifilar wire on the catheter and then heated to cause the tubing to shrink, transferring heat to and melting the coating on the wire and applying pressure to form the coating as it flows.
Figure 10:
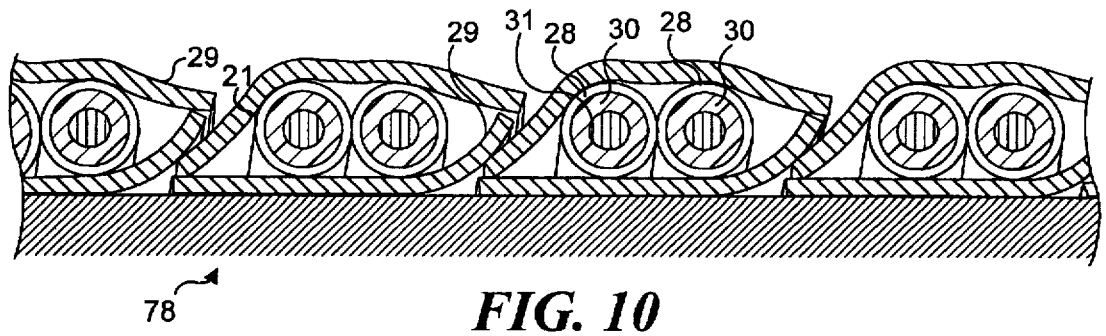
FIG. 10 is a cross-sectional view of the embodiment of FIG. 6, showing a catheter wound with overlapping layers of plastic tape, wire, and plastic tape.

The third method for heating and forming the PVC material on the bifilar wire coils is illustrated in regard to an exemplary embodiment 78 shown in FIG. 9. This embodiment was produced by coiling coated bifilar wire 21 helically around catheter 10, just as shown FIG. 4. However, to form embodiment 78, the helical coils of bifilar wire with the extruded PVC coating are covered by a section of a heat-shrink tube 80, which is sufficiently long to completely cover the bifilar wire coil comprising the heater coil. The diameter of the section of heat-shrink tube 80 is selected so that the heat-shrink tube readily slides over the external diameter of the bifilar wire coil. Once the heat-shrink tube is positioned over the helical coils, heat is applied to cause the diameter of the heat-shrink tubing to decrease. The heat-shrink tubing conducts the heat to the PVC coating on the bifilar wire, causing the coating to melt and flow and applies pressure uniformly to form the melted PVC coating on the wire so that it has a generally smooth outer surface. Heat is applied to melt the PVC coating on the bifilar wire and shrink the heat-shrink tube with a hot air source or an infra-red source (neither shown). A suitable heat-shrink material for the tubing in this embodiment is one that will not bond to the PVC coating or catheter surface when the heat is applied to shrink the material. For example, type FIT 221 polyolefin tubing, from Alpha Wire Corporation, Elizabeth, N.J., can be used for the heat-shrink tube. Once the PVC coating has been melted and formed by the shrinking heat-shrink tubing, the heat-shrink tubing is removed from the heater coil.

Figure 6:
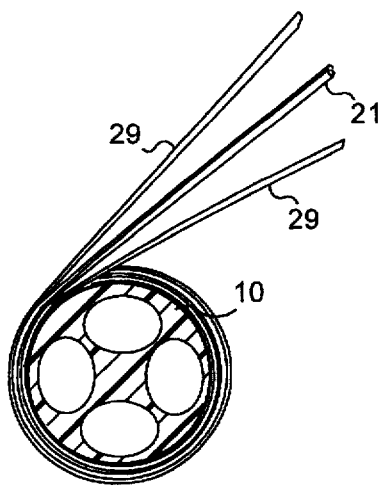
FIG. 6 is a transverse cross-sectional view of the catheter, showing how the bifilar wire and two layers of tape are helically wound onto the outer surface of the catheter.

Instead of using a coated lead, bifilar wire 21 can be helically coiled around catheter 10 with two layers of a PVC tape 29, as shown in FIG. 6. Preferably, the two runs of PVC tape with bifilar wire 21 sandwiched between are helically coiled in line onto the catheter from three separate spools (not shown) that are wound around catheter 10. It is preferable to simultaneously wrap the PVC tape and the bifilar wire around the catheter; however, the PVC tape layers and bifilar wire can instead be separately coiled onto the catheter, with the helical coils of the PVC tape layers and bifilar wire running in the same or alternating helical directions. Alternatively, a PVC film (not shown) can be wrapped in line with the helical coils of the bifilar wire.

The section of the catheter around which the coiled bifilar wire and PVC tape/film has been applied is then heated above the melting point of the PVC material using either of the three methods described above, causing the PVC tape/film to melt, flow into the voids between the coils of bifilar wire 21, and bond to the outer surface of catheter 10. The result appears similar to embodiment 22 shown in FIG. 5 (although formed in a different manner). A smoother outer surface can be produced by coiling the bifilar wire and PVC material so that the gap between adjacent coils of the bifilar wire is minimized. The PVC tape/film bonds to the bifilar wire when melted, filling the gaps between the adjacent coils, forming a smooth coating around the coils of the bifilar wire, and bonding to the catheter between the coils and at each end of the helical coil to hold the heater coil in place on the catheter.

Figure 7:
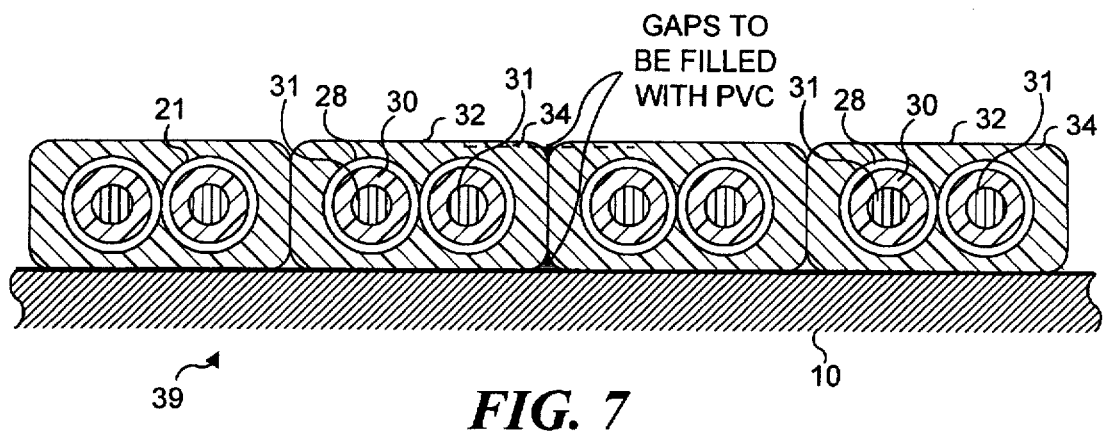
FIG. 7 is a cross-sectional view of another embodiment in which the coating applied to the bifilar wires has a generally quadrilateral cross-sectional shape.

In FIGS. 7 and 8, an embodiment 39 is shown that uses an extruded PVC coating having a different cross-sectional shape than embodiment 22 in FIG. 4. FIG. 7 shows embodiment 39 before the PVC coating applied to bifilar wire 21 is melted, and in FIG. 8, the embodiment is shown after the PVC coating has been melted, forming a smooth PVC coating 34'. To produce embodiment 39, a coated lead 32 is formed for fabricating heater 12 using an extrusion process that yields a quadrilateral or rectangular shape coating with rounded corners (see FIG. 7). This embodiment has an advantage over embodiment 22, since the gap between adjacent wraps of coated lead 32 comprises only the relatively small V-shaped notches formed at the rounded corners. The "V-shaped" notches formed adjacent the outer surface of catheter 10 and at the radially outer corners of two adjacent wraps of coated lead 32 (indicated by the horizontal cross-hatch lines in the Figure) have substantially less volume than the void between adjacent wraps of the coated lead in the first embodiment. As a result, when PVC coating 34 is heated above its melting temperature, the melted PVC has only a small volume to fill when it flows and bonds to the catheter, producing a smoother outer surface, as shown in FIG. 8, compared to the outer surface of PVC coating 34'. The rectangular shape of coated lead 32 has another advantage, since it is easier to wrap the rectangularly-shaped lead around catheter 10 and maintain the side-by-side relationship of conductors 31. It will be apparent that the rectangular shape of coated lead 32 is more readily retained in flat contact with the outer surface of catheter 10 during the fabrication and coiling process. However, it is more difficult to extrude PVC coating 34 to produce coated lead 32 with a rectangular shape than with the oblate spheroid shape of coated lead 24, which is used in the first embodiment.

Once coated lead 32 is wrapped around the exterior surface of catheter 10 to form heater 12 of the required length, heat is applied to melt PVC coating 34 using one of the three techniques described above. The PVC coating flows into the notches between adjacent wraps and bonds to catheter 10, just as described above in connection with the first embodiment.

Although the present invention has been described in connection with the preferred form of practicing it, it will be understood by those of ordinary skill in the art that many modifications can be made thereto within the scope of the claims that follow. Accordingly, it is not intended that the scope of the invention in any way be limited by the above description, but that it be determined entirely by reference to the claims that follow.

The invention in which an exclusive right is claimed is defined by the following:

1. A method for making a heater for a catheter that is employed to monitor cardiac output, comprising the steps of:

(a) providing a catheter having at least one lumen adapted to accept a heater lead;

(b) coating a wire with a thermoplastic material to form a coated lead;

(c) winding the coated lead around the catheter to form a heater coil, said heater coil having gaps between adjacent coils of the coated lead; and (d) elevating the temperature of the heater coil above a melting temperature of the thermoplastic material, causing said material to flow into and fill the gaps between adjacent coils of the coated lead and bonding the heater coil to the catheter.

2. The method of claim 1, wherein the adjacent coils of the coated lead do not contact each other when the heater coil is wound, and wherein when the thermoplastic material melts, said material flows into and fills the gaps to form a generally smooth outer surface on the heater coil.

3. The method of claim 1, wherein the adjacent coils of coated lead contact each other when the heater coil is wound, said gaps comprising notches disposed adjacent the surface of the catheter and outwardly of points where the coils of the coated lead contact each other, and wherein when the thermoplastic material melts, said material flows into the notches to form a generally smooth outer surface on the heater coil.

4. The method of claim 1, wherein the coated lead has a generally circular cross-sectional shape.

5. The method of claim 1, wherein the coated lead has a generally quadrilateral cross-sectional shape.

6. The method of claim 1, wherein the wire that is coated comprises a bifilar wire.

7. The method of claim 1, wherein the step of elevating the temperature comprises the steps of.
  (a) positioning a heat-shrink tube over the heater coil;
  (b) applying heat to the heat-shrink tube to elevate the temperature of the heater coil above the melting temperature of the thermoplastic material via conduction of the heat through heat-shrink tubing and to shrink the heat-shrink tubing to form the thermoplastic material as said material melts; and
  (c) removing the heat-shrink tubing from the heater coil after the thermoplastic material cools.

8. A method for attaching a heater to a catheter comprising the steps of:
  (a) winding an insulated heater wire around an exterior surface of the catheter;
  (b) applying a plastic material over the insulated heater wire;
  (c) subjecting the plastic material to an elevated temperature so that the plastic material experiences a change in state and secures the insulated heater wire to the exterior surface of the catheter; and
  (d) cooling the plastic material to an ambient temperature.

9. The method of claim 8, wherein the step of winding the insulated heater wire comprises the step of forming a plurality of helical windings of the insulated heater wire around the exterior surface of the catheter, adjacent helical windings having a notch between them.

10. The method of claim 9, wherein a predetermined distance between the adjacent helical windings is selected so that a cross-sectional area of a gap formed between adjacent windings of the insulated heater wire is less than a cross-sectional area of a portion of the plastic material disposed radially beyond the insulated heater wire in the helical winding, said portion of the plastic material flowing into and substantially filling the gap between the adjacent helical windings when heated.

11. The method of claim 9, wherein the plastic material is applied to the insulated heater wire by wrapping the plastic material to form a layer over an outer diameter of the helical windings.

12. The method of claim 8, wherein the plastic material comprises polyvinyl chloride (PVC), and wherein a characteristic melting temperature of the PVC is less than or equal to a melting temperature of a material comprising the catheter.

13. The method of claim 8, wherein the insulated heater wire comprises a pair of conductors, said conductors comprising the pair extending substantially parallel to each other, each conductor being covered with an insulating sheath, said insulating sheath of each conductor being bonded together along a line extending longitudinally along the insulating sheath.

14. The method of claim 8, wherein the step of subjecting the plastic material to the elevated temperature comprises the steps of electrically coupling the insulated heater wire to a source of an electrical current; and, causing the electrical current to flow through the insulated heater wire, said electrical current heating the insulated heater wire above a characteristic melting temperature of the plastic material to cause the change in state.

15. The method of claim 8, wherein the step of subjecting the plastic material to the elevated temperature comprises the step of applying an external source of heat to the plastic material, said external source of heat transferring heat to the plastic material so that the temperature of the plastic material effects the change in state.

16. The method of claim 9, further comprising the step of enclosing the catheter with the insulated heater wire wound around the catheter in a mold prior to subjecting the plastic material to the elevated temperature, said mold forcing the plastic material to flow into the gap between the adjacent helical windings.

17. A method for producing a coiled conductor having a substantially smooth surface, on an exterior of a catheter, said method comprising the steps of:
  (a) extruded a thermoplastic coating on a wire, said thermoplastic coating being selected in part for its characteristic melting temperature, said wire having an electrically insulating layer that is substantially covered by the thermoplastic coating;
  (b) coiling the wire covered by the thermoplastic coating around the catheter, forming a plurality of adjacent coils; and
  (c) heating the thermoplastic coating on the wire that is coiled above its characteristic melting temperature, causing the thermoplastic coating to melt and flow, forming a substantially smooth outer surface over the adjacent coils and adhering the wire to the catheter.

18. The method of claim 17, wherein the wire is bifilar, comprising a pair of side-by-side conductors, separately covered with the insulation.

19. The method of claim 17, wherein the step of heating the wire, comprises the step of enclosing the catheter with the wire coiled around it in a mold, and wherein heat is applied externally to the mold.

20. The method of claim 17, wherein the step of heating comprises the steps of attaching a source of electrical current to the wire, and enabling sufficient electrical current to flow through the wire to increase its temperature above the characteristic melting point of the thermoplastic coating.

21. The method of claim 17, wherein the step of heating comprises the steps of:
  (a) positioning a heat-shrink tube around the adjacent coils of the wire;
  (b) heating the heat-shrink tube, causing it to shrink around the coils of the wire, heat being transferred through the heat-shrink tubing to the thermoplastic coating to raise said coating above its melting temperature, and said heat-shrink tube shrinking around the thermoplastic coating to form it around the coils of the wire; and (c) removing the heat-shrink tube after the thermoplastic coating has cooled.

22. A method for securing a heater on an exterior of a catheter, said method comprising the steps of:

(a) coiling an insulated wire around an outer surface of the catheter, forming a plurality of adjacent coils;

(b) covering the coils of the insulated wire with a plastic material; and (c) heating the plastic material to an elevated temperature so as to cause the plastic material to change state and form around the outer surface of the coils, said plastic material thereby securing the insulated wire to the outer surface of the catheter.

23. The method of claim 22, wherein the plastic material comprises a heat-shrink material that shrinks when heated to the elevated material, shrinkage of the heat-shrink material comprising the change of state.

24. The method of claim 23, wherein the heat-shrink material comprises a tube that is slipped over the coils of the insulated wire, and which is shrunk tightly around the wire when heated to the elevated temperature.

25. The method of claim 23, wherein the heat-shrink material is heated to the elevated temperature with hot air.

26. The method of claim 22, wherein the plastic material comprises a tape that is wrapped around the coils of the insulated wire, said tape being melted when heated to the elevated temperature and flowing around the coils and bonding to the outer surface of the catheter.

* * * * *